United States Patent [19]

King et al.

[11] Patent Number: 5,391,803

[45] Date of Patent: Feb. 21, 1995

[54] PRODUCTION OF DIMETHYL CARBONATE USING COPPER ZEOLITE CATALYSTS

[75] Inventors: Stanley S. T. King; Mark E. Jones; Michael M. Olken, all of Midland, Mich.

[73] Assignee: The Dow Chemical Company, Midland, Mich.

[21] Appl. No.: 176,744

[22] Filed: Jan. 3, 1994

Related U.S. Application Data

[63] Continuation-in-part of Ser. No. 954,771, Sep. 30, 1992, abandoned.

[51] Int. Cl.$^6$ .............................................. C07C 69/96
[52] U.S. Cl. ...................................... 558/277; 558/260
[58] Field of Search ............................................ 558/277

[56] References Cited

U.S. PATENT DOCUMENTS

| | | | |
|---|---|---|---|
| 3,846,468 | 11/1974 | Perrotti et al. | 260/463 |
| 3,980,690 | 9/1976 | Cipriani et al. | 260/463 |
| 3,994,960 | 11/1976 | Yamazaki et al. | 260/485 R |
| 4,218,391 | 8/1980 | Romano et al. | 260/463 |
| 4,318,862 | 3/1982 | Romano et al. | 260/463 |
| 4,612,387 | 9/1986 | Feitler | 560/232 |
| 4,689,422 | 8/1987 | Sawicki et al. | 558/277 |
| 4,691,041 | 9/1987 | Duranleau et al. | 558/277 |
| 4,879,266 | 11/1989 | Bhattacharya | 502/164 |
| 4,900,705 | 2/1990 | Sawicki et al. | 502/158 |
| 4,917,711 | 4/1990 | Xie et al. | 55/68 |
| 5,004,827 | 4/1991 | Curnutt | 558/277 |

FOREIGN PATENT DOCUMENTS 0429675 6/1990 European Pat. Off.

OTHER PUBLICATIONS

Lee et al., "Alkylcarbonate Synthesis by New Catalytic System," *Dioxygen Activation and Homogeneous Catalytic Oxidation*, pp. 631–640, 1991.

Primary Examiner—José G. Dees
Assistant Examiner—Dwayne C. Jones
Attorney, Agent, or Firm—Robert M. O'Keefe

[57] ABSTRACT

A process for producing dialkyl carbonates which comprises contacting an alkanol, carbon monoxide, and oxygen with a catalyst to produce dialkyl carbonate, the catalyst having been prepared by heating a solid copper compound in the presence of a zeolite to form a zeolite containing copper.

9 Claims, No Drawings

PRODUCTION OF DIMETHYL CARBONATE USING COPPER ZEOLITE CATALYSTS

This application is a continuation-in-part of U.S. application Ser. No. 07/954,771, filed Sep. 30, 1992, now abandoned.

BACKGROUND OF THE INVENTION

This invention relates to gas phase production of dialkyl carbonates from methanol, oxygen, and carbon monoxide.

Dimethyl carbonate is a valuable commercial product finding utility as a precursor to polycarbonates and isocyanates, as a solvent, and as a gasoline fuel additive.

Park and Lee report in *Dioxygen Activation and Homogeneous Catalytic Oxidation*, pages 631–640 (1991), that copper ion-exchanged Y zeolite was employed in a liquid phase reaction to produce dimethyl carbonate from methanol, carbon monoxide, and oxygen. While this catalyst brings about formation of dimethyl carbonate in a liquid phase reaction, this type of catalyst is not an effective catalyst when employed in a gas phase reaction. Since liquid phase reactions are oftentimes unattractive due to the corrosiveness of the reactants and products, it would be desirable to find an effective gas phase process for the production of dialkyl carbonates such as dimethyl carbonate.

SUMMARY OF INVENTION

This invention, in one respect is a gas phase process for producing dialkyl carbonates which comprises contacting an alkanol, carbon monoxide, and oxygen with a catalyst to produce dialkyl carbonate, the catalyst having been prepared by heating a solid copper compound in the presence of a zeolite to form a zeolite containing copper.

DETAILED DESCRIPTION OF THE INVENTION

The catalyst used in this invention comprises copper and a zeolite support. The catalyst is made by heating a solid copper compound in the presence of a zeolite to form a zeolite containing copper, with or without intimate contact of the solid copper compound and zeolite during the heating step. The catalyst can be prepared as described in U.S. Pat. No. 4,917,711, incorporated herein by reference.

The zeolites useful in this invention include any of the known zeolites. Zeolites have the advantage that they do not combust in the process of this invention, wherein oxygen is present. The starting zeolite can be selected in an acid form or in a salt form, wherein the cation is typically an ion from the Group IA or IIA metals, such as sodium or magnesium ions. Examples of suitable zeolites include zeolite rho, zeolite L, zeolite beta, zeolite omega, faujasites such as Y zeolite, and mordenite. The zeolites can have a framework silica/alumina molar ratio of from about 1:1 to about 2000:1. A preferred zeolite has a framework silica/alumina molar ratio of about 2:1 to about 30:1. More preferably, the framework silica/alumina molar ratio is from about 7:1 to about 25:1. The zeolites can have a bulk silica/alumina molar ratio of from about 1:1 to about 2000:1. Preferred bulk silica/alumina molar ratios are from about 2:1 to about 30:1. More preferably, the bulk silica/alumina molar ratio is from about 5:1 to about 25:1. It has been found that the ratio of the framework to bulk silica/alumina molar ratios have a significant impact on the performance of the catalyst. The relative amounts of framework to bulk silica/alumina molar ratio is readily determined by skilled artisans. Generally, the ratio of framework to bulk silica/alumina molar ratios can be in the range from about 1:1 to about 5:1. Preferably, the ratio of framework to bulk silica/alumina molar ratios is less than about 3:1, more preferably less than about 2:1, and most preferably less than about 1.3:1. Among the zeolites, faujasite, and mordenite are preferred. Most preferably, the zeolite is Y zeolite. The most preferred Y zeolite has a framework silica/alumina molar ratio of about 12:1 and a bulk silica/alumina molar ratio of about 11:1. An Y example of a commercially available, most preferred zeolite is sold by United Oil Products Company under the name LZ-Y-85.

The copper compound used in the practice of this invention to form the catalyst can be any salt of copper that is capable of dispersing onto the zeolite when heated. Examples of suitable copper compounds include cupric chloride, cupric nitrate, cupric oxide, cuprous chloride, cuprous nitrate, and cuprous oxide. Preferred copper compounds include cupric chloride, cuprous chloride, and cupric oxide. More preferred copper compounds are cupric chloride and cuprous chloride.

The catalyst of this invention is prepared by heating a solid copper compound in the presence of zeolite, with or without intimate contact of the zeolite and solid copper compound. The copper compound and zeolite must be within a certain maximum distance to allow the copper compound to reach the zeolite support, this distance being readily determined by skilled artisans. If the catalyst of this invention is prepared by having the starting materials in intimate contact, the catalyst is prepared by thoroughly mixing, typically by mechanical mixing, a zeolite and a copper compound and then heating the admixture to form a zeolite containing copper. While the copper compound can be in any form, it is preferred to start with powder to facilitate rapid formation of the copper containing zeolite catalyst, as well as to facilitate rapid mixing of the starting materials when in intimate contact. The heating temperature is generally greater than about 20° C., preferably greater than about 50° C., more preferably greater than about 100° C., and most preferably greater than about 250° C. The heating temperature is generally less than about 1000° C., preferably less than about 900° C., and most preferably less than about 800° C. The heating can be carried out under any atmosphere at which the copper containing zeolite catalyst is formed. While the heating can be carried out in air at low temperature, it is preferred to carry out the heating in an inert atmosphere such as under helium, nitrogen, or carbon dioxide at any temperature. A reducing atmosphere, preferably ammonia, can be employed when the copper compound is a copper oxide. Following reduction with ammonia, however, the catalyst should be heated under a flow of inert gas at a temperature of at least about 150° C. and less than about 500° C. to strip off excess ammonia. The amount of time the heating is carried out can vary widely depending on such factors as ratio of copper compound to zeolite and temperature, the amount of copper compound desired in the final catalyst and temperature, but is typically from about 15 minutes to about 7 days, preferably from about 1 hour to about 3 days. When the starting materials are in intimate contact, it is preferred to heat until no copper compound is seen on visual inspection. The weight percentage of copper compound in the final copper containing zeolite catalyst can be from about 0.1 to 99.9 percent, preferably from about 1 to about 50 percent, more preferably from about 1 to about 25, and most preferably from about 10 to about 25 percent. The catalyst obtained from the preparations described above can be used as is or can be shaped into a variety of well known physical shapes. For example, the catalyst can be shaped into pellets or spheroids. In addition, well known binders can be used such as silica, alumina, and mixtures thereof. A catalyst prepared as described above requires no further treatment.

The catalyst employed in the process of the present invention preferably contains less than 10 percent water, more preferably less than 6 percent water, and most preferably less than 3 percent water. Water can be removed from the catalyst prior to use by heating or can be removed in situ during the process of this invention.

In the process of this invention for producing dialkyl carbonates, an alkanol, carbon monoxide, and oxygen are contacted with catalyst. Alkanols useful in this invention include alkanols which are gaseous under reaction conditions. Preferred alcohols correspond to the formula ROH wherein R is $C_{1-6}$ alkyl or $C_{3-6}$ cycloalkyl. R is preferably $C_{1-6}$ alkyl. Examples of preferred alkanols include methanol, ethanol, propanol, butanol, pentanol, hexanol, cyclopropanol, cyclobutanol, cyclopentanol, and cyclohexanol. More preferably, the alkanol is methanol, ethanol, or propanol. Most preferably, the alkanol is methanol.

The process of this invention prepares dialkyl carbonates of the formula: RO—CO—OR wherein R is $C_{1-6}$ alkyl or $C_{3-6}$ cycloalkyl, preferably is $C_{1-6}$ alkyl, more preferably is methyl, ethyl, or propyl, and most preferably is methyl. Examples of dialkyl carbonates prepared by the process of this invention include dimethyl carbonate, diethyl carbonate, dipropyl carbonate, dibutyl carbonate, dipentyl carbonate, dihexyl carbonate, dicyclopropyl carbonate, dicyclobutyl carbonate, dicyclopentyl carbonate, and dicyclohexyl carbonate. Preferred dialkyl carbonates prepared in accordance with this invention include dimethyl carbonate, diethyl carbonate, dipropyl carbonate, dibutyl carbonate, dipentyl carbonate, and dihexyl carbonate. More preferred products are dimethyl carbonate, diethyl carbonate, and dipropyl carbonate. The most preferred product of this invention is dimethyl carbonate.

In general, the alkanol is contacted with oxygen and carbon monoxide under sufficient conditions so as to prepare a dialkyl carbonate.

The process of this invention involves contacting carbon monoxide, oxygen and an alcohol in the gas phase and passing them over the catalyst described hereinbefore. The process of this invention can be illustrated by the equation

$$2ROH + \tfrac{1}{2}O_2 + CO \longrightarrow R-O\overset{\overset{O}{\|}}{C}O-R + H_2O$$

wherein R is as defined hereinbefore. The ratio of carbon monoxide to the alkanol can be any mole ratio which results in the preparation of the dialkyl carbonates. Preferably, the mole ratio of carbon monoxide to the alkanol is between about 1000:1 and about 1:1000. More preferably, the mole ratio of carbon monoxide to alkanol is between about 100:1 and about 1:100, and most preferably, the mole ratio of carbon monoxide to alkanol is between about 10:1 and about 1:10. The mole ratio of oxygen to alkanol is any ratio which results in the preparation of the dialkyl carbonates. Preferably, the mole ratio of oxygen to alkanol is between about 1000:1 and about 1:1000. More preferably, the mole ratio of oxygen to alkanol is between about 100:1 and about 1:100. Most preferably, the mole ratio of oxygen to alcohol is between about 10:1 and about 1:10. The mole ratio of oxygen to carbon monoxide is any ratio which results in the preparation of the dialkyl carbonates. Preferably, the mole ratio of oxygen to carbon monoxide is between about 1000:1 and about 1:1000. More preferably, the mole ratio of oxygen to carbon monoxide is between about 100:1 and about 1:100, and most preferably, the mole ratio of oxygen to carbon monoxide is between about 10:1 and about 1:10.

The oxygen can be added to the reaction mixture as pure molecular oxygen or diluted with an inert gas such as nitrogen, helium, argon, and carbon dioxide.

This process can be performed at any temperature and pressure at which the reaction proceeds. Preferred temperatures are between about 20° C. and about 350° C., with between about 90° C. and about 250° C. being more preferred. The pressure can be atmospheric or superatmospheric pressure. Preferred pressures are between about 1 and about 100 atmospheres, with between about 1 and about 50 atmospheres being most preferred.

The reaction mixture feed gas flow rate, expressed as gas hourly space velocity (GHSV), can be between about 100 $hr^{-1}$ and about 50,000 $hr^{-1}$ and most preferably between about 500 $hr^{-1}$ and about 2,000 $hr^{-1}$.

The dialkyl carbonate can be recovered from the reaction mixture by methods well known in the art, such as by azeotropic distillation, extractive distillation and simple distillation.

The process of this invention can be performed in either a fixed or fluid bed reactor using either continuous or batch processing methods. It is preferred to use a fixed bed reactor and a continuous mode of operation.

The process of this invention produces high gas phase conversions and yields based on converted methanol. Another useful means for describing the efficacy of the process is by "productivity". As used herein, "productivity" is defined as the pounds of a particular product produced per cubic foot of catalyst per hour ($lb/ft^3/hr$). In the practice of this invention, productivity is greater than about 1 $lb/ft^3/hr$. More preferably, the productivity is greater than about 2 $lb/ft^3/hr$. Even more preferably, the productivity is greater than about 4 $lb/ft^3/hr$. Most preferably, the productivity of the process of this invention is greater than about 5 $lb/ft^3/hr$.

As used herein, "selectivity to DMC" means the percentage of the total moles of DMC produced divided by the sum of the moles of all organic products produced which contain carbon, oxygen, and hydrogen.

The following examples are included for the purposes of illustration only and are not to be construed to limit the scope of the invention or claims. Unless otherwise indicated, all parts and percentages are by weight.

EXAMPLE 1

Preparation of Catalyst A and Production of Dimethylcarbonate Using Catalyst A

A catalyst was prepared by heating a solid mixture containing 25 weight percent of cuprous chloride and a hydrogen Y zeolite having a framework silica/alumina molar ratio of 12:1 and a bulk silica/alumina molar ratio of 10.9:1 (LZ-Y-85, UOP Industries) at 650° C. in nitrogen for 48 hours. This catalyst is designated "Catalyst A".

About 0.6 cc of Catalyst A was heated in a ¼" quartz tube to 130° C. A mixture of methanol/CO/O$_2$/N$_2$ having a mole ratio of 0.88/4/0.5/2 was flowed over Catalyst A at a GHSV of 870 hr$^{-1}$. The products were analyzed using on-line gas chromotography. The selectivity to DMC in the organic products was 80 percent after 10 and 20 hours. The initial productivity to DMC was 4 lbs/ft$^3$/hr and was 4 lbs/ft$^3$/hr after 12 hours.

EXAMPLE 2

Preparation of Catalyst B and Production of Dimethylcarbonate Using Catalyst B

Pellets of hydrogen Y zeolite (LZ-Y-85, UOP Industries) (without binder) and an open vessel containing cupric chloride were placed in a closed tube having a helium inlet and a port for helium release. Then, hot helium (480° C.) was flowed through the system to carry cuprous chloride vapor over the zeolite for 24 hours. Next, the system was heated at 650° C. under helium purge for 24 hours. The resulting catalyst contained approximately 8.4 percent by weight copper and is designated "Catalyst B".

About 0.6 cc of Catalyst B was heated in a ¼" quartz tube to 130° C. A mixture of CO/air/methanol having a mole ratio of 1.8/1.1/1 was flowed over Catalyst B at a GHSV of 870 hr$^{-1}$. The products were analyzed using an on-line GC. Catalyst B initially converted 5 percent methanol to DMC, 5.0 percent after 20 hours, 5.0 percent after 40 hours. 5.0 percent after 60 hours, and 4.9 percent after 80 hours.

EXAMPLE 3

Preparation of Catalyst C and Production of Dimethylcarbonate Using Catalyst C

A hydrogen Y zeolite powder having a bulk silica/alumina mole ratio of 15:1 and a framework silica/alumina mole ratio of 22:1 (LZ-20M, UOP Industries) was mixed with cuprous chloride powder and pelletized. The pellets were heated at 650° C. under helium for 63 hours. The resulting catalyst contained approximately 7.3 percent copper is designated "Catalyst C". Catalyst C was employed in the reaction procedure described in Example 2 to form DMC and initially converted 3.0 percent methanol to DMC, 3.4 percent after 20 hours, 3.4 percent after 40 hours, and 3.3 percent after 60 hours.

EXAMPLE 4

Preparation of Catalyst D and Production of Dimethylcarbonate Using Catalyst D

Pellets of a hydrogen Y zeolite (with 20 percent alumina binder) having a bulk silica/alumina molar ratio of 5.2:1 and a framework silica/alumina molar ratio of approximately 9:1 (LZ-Y-84, UOP Industries) and cuprous chloride vapor were heated at 600° C. for one hour using the procedure of Example 2 to form a catalyst having approximately 7.6 percent copper based on the zeolite (6.2 weight percent based on the entire catalyst). This catalyst is designated "Catalyst D". Catalyst D was employed in the reaction procedure described in Example 2 to form DMC and initially converted 3.2 percent methanol to DMC and 3.2 percent after 20 hours on stream.

EXAMPLE 5

Preparation of Catalyst E and Production of Dimethylcarbonate Using Catalyst E

Pellets of a hydrogen Y zeolite (without binder) having a bulk silica/alumina molar ratio of 6:1 (HSZ-330-HSA, TOSOH Corporation) were heated with cuprous chloride vapors at 550° C. for one hour using the procedure described in Example 2. This catalyst is designated "Catalyst E". Catalyst E was employed in the reaction procedure described in Example 2 to form DMC. Catalyst E initally converted 3.0 percent methanol to DMC, 2.9 percent after 20 hours, and 2.8 percent after 40 hours.

EXAMPLE 6

Preparation of Catalyst F and Production of Dimethylcarbonate Using Catalyst F

The powder of the hydrogen Y zeolite used in Example 3 (LZ-20M, UOP Industries) and cuprous oxide were mixed to yield an admixture containing 21.3 percent cupric oxide. The admixture was pelletized and then heated at 650° C. for 70 hours under a helium purge. The resulting catalyst is designated "Catalyst F". Catalyst F was employed in the reaction to form DMC as described in Example 2. Catalyst F initally converted 2.2 percent methanol to DMC which stayed relatively constant after 10 hours on stream.

EXAMPLE 7

Preparation of Catalyst G and Production of Dimethylcarbonate Using Catalyst G

A powder mixture containing 80 weight percent sodium Y zeolite (HSZ-320NAA, TOSOH USA, Inc.) having an estimated bulk silica/alumina molar ratio of 5.5:1 and a framework silica/alumina molar ratio of approximately 7:1, the framework ratio being estimated based on the unit cell dimensions reported by the manufacturer, and 20 weight percent cuprous chloride was heated in nitrogen at 650° C. for three hours. This mixed powder was washed with water and dried at room temperature. This catalyst is designated "Catalyst G". The powder was pressed into 14–30 mesh pellets which were packed in a 5 cc ASTELLOY-C ™ tubular reactor. A feed mixture of CO/methanol/oxygen/nitrogen (mole ratio of 18.2/9.1/1/21.7) was introduced into the reactor with a total gas flow rate of 350 cc/min (GHSV of 4,200 h$^{-1}$). A temperature of 130° C. and a pressure of 300 psig was maintained in the reactor. A productivity to DMC of 4.4 lbs/ft$^3$/hr and a selectivity to DMC of 80.3 percent was produced using Catalyst G.

EXAMPLE 8

Preparation of Catalyst H Based on Zeolite Rho Production of Dimethylcarbonate Using Catalyst H In a one liter plastic container were dissolved 160.03 g of NaOH in 250 mL of water. To the sodium hydroxide solution was stirred in 138.11 g of Al$_2$O$_3$.H$_2$O (Catapal B, VISTA) and water was then added to bring the total volume up to 500 mL. Next, the mixture was heated in an oven at 100° C. in a closed container until the solution was clear (approximately 12 hours) to thereby produce a 4M Na$_2$AlO$_2$OH aqueous solution. In a two liter plastic container was mixed 200 mL of the $Na_2AlO_2OH$ aqueous solution and 56 mL of CsOH (Aldrich, 99.9% pure, 50% aq., d=1.762). Then, 32 g of NaOH was dissolved in the mixture. With vigorous stirring was then added 720 mL of colloidal silica (LS-30 Ludox, 30% aq. d=1.21, I.E. Du Pont de Nemours Co). The resulting solution was allowed to cold age at room temperature for six days. Then, the aged solution was reacted in an air oven at 100° C. for six days. The solid was filtered and washed with distilled water to yield a final composition of the empirical formula $Na_8Cs_4Al_{12}Si_{36}O_{96}$. This material was exchanged five times with 2M ammonium nitrate aqueous solution at 100° C. until the Cs level was less than 1 in the empirical formula. The resulting ammonium rho zeolite was heated under air at 500° C. for four hours to provide a hydrogen rho zeolite.

A powder mixture containing 80 weight percent hydrogen rho zeolite powder and 20 weight percent cuprous chloride was heated in nitrogen at 650° C. for three hours. The powder was pressed into 14×30 mesh pellets, designated Catalyst H, which were packed in a 5cc ASTELLOY-C™ reactor. A feed mixture of CO/methanol/oxygen/nitrogen (mole ratio 18.2/9.1/1/21.7) was introduced into the reactor with a total gas flow rate of 350 cc/min (GHSV of 4200 $hr^{-1}$). A temperature of 130° C. and a pressure of 300 psig was maintained in the reactor. A productivity of 0.84 $lbs/ft^3/hr$ and a selectivity to DMC of 70.0 percent was produced.

What is claimed is:

1. A gas phase process for producing dialkyl carbonates which comprises contacting an alkanol, carbon monoxide, and oxygen with a catalyst to produce dialkyl carbonate, the catalyst having been prepared by heating a solid copper compound in the presence of a zeolite to form a zeolite containing copper.

2. The process of claim 1 wherein the zeolite is a hydrogen or a Group IA or IIA Y zeolite having a bulk silica/alumina molar ratio of from about 2:1 to about 30:1, and a framework silica/alumina molar ratio of from about 2:1 to about 30:1, and a ratio of framework to bulk silica/alumina molar ratios of from about 1:1 to about 2:1.

3. The process of claim 2 wherein the bulk silica/alumina molar ratio of the Y zeolite is from about 5:1 to about 25:1, the framework silica/alumina molar ratio of from about 9:1 to about 25:1, and the ratio of framework to bulk silica/alumina molar ratios of from about 1:1 to about 1.3:1.

4. The process of claim 3 wherein the alkanol is methanol, ethanol, or propanol.

5. The process of claim 4 wherein the alkanol is methanol.

6. The process of claim 4 wherein the contacting temperature is from about 20° C. to about 350° C.

7. The process of claim 6 wherein the contacting temperature is from about 90° C. to about 250° C.

8. The process of claim 6 wherein the alkanol, carbon monoxide, and oxygen have a gas hourly space velocity of from about 100 $hr^{-1}$ to about 50,000 $hr^{-1}$.

9. A gas phase process for producing dimethyl carbonate which comprises contacting methanol, carbon monoxide, and oxygen with a catalyst at a temperature of from about 90° C. to about 250° C. to produce dimethyl carbonate, the catalyst having been prepared by heating a solid copper compound in the presence of a Y zeolite to form a Y zeolite containing copper, wherein the Y zeolite has a bulk silica/alumina molar ratio of from about 5:1 to about 25:1, a framework silica/alumina molar ratio of from about 9:1 to about 25:1, and a ratio of framework to bulk silica/alumina molar ratios of from about 1:1 to about 1.3:1; and wherein the methanol, carbon monoxide, and oxygen have a gas hourly space velocity of from about 500 $hr^{-1}$ to about 2,000 $hr^{-1}$.

* * * * *